United States Patent
Kamohara et al.

(10) Patent No.: US 7,172,338 B2
(45) Date of Patent: Feb. 6, 2007

(54) STIRRING MIXER FOR DENTAL IMPRESSION MATERIAL

(75) Inventors: Hiroshi Kamohara, Tokyo (JP); Nobutaka Watanabe, Tokyo (JP)

(73) Assignee: GC Corporation, Tokyo (JP)

( * ) Notice: Subject to any disclaimer, the term of this patent is extended or adjusted under 35 U.S.C. 154(b) by 374 days.

(21) Appl. No.: 10/923,738

(22) Filed: Aug. 24, 2004

(65) Prior Publication Data
US 2005/0048437 A1    Mar. 3, 2005

(30) Foreign Application Priority Data
Sep. 1, 2003   (JP)  ............................ 2003-308701

(51) Int. Cl.
*B01F 7/00*   (2006.01)
(52) U.S. Cl. ................. 366/329.1; 222/145.6
(58) Field of Classification Search ............ 366/172.1, 366/172.2, 176.1, 181.5, 325.1, 325.2, 326.1, 366/329.1, 329.2; 222/145.5, 145.6
See application file for complete search history.

(56) References Cited

U.S. PATENT DOCUMENTS

| | | | |
|---|---|---|---|
| 5,249,862 A | | 10/1993 | Herold et al. |
| 6,244,740 B1 * | | 6/2001 | Wagner et al. ............ 366/181.5 |
| 6,394,643 B1 * | | 5/2002 | Bublewitz et al. ........ 366/172.1 |
| 6,443,612 B1 * | | 9/2002 | Keller ........................ 366/307 |
| 6,523,992 B1 * | | 2/2003 | Bublewitz et al. ........ 366/172.1 |
| 6,540,395 B2 | | 4/2003 | Muehlbauer et al. |
| 6,837,612 B2 * | | 1/2005 | Bublewitz et al. ........ 366/172.1 |
| 6,932,243 B2 * | | 8/2005 | Keller ........................ 222/145.6 |
| 2004/0085854 A1 * | | 5/2004 | Pauser et al. ............ 366/172.1 |
| 2005/0048437 A1 * | | 3/2005 | Kamohara et al. ............ 433/89 |
| 2005/0226095 A1 * | | 10/2005 | Wagner et al. .............. 366/194 |

FOREIGN PATENT DOCUMENTS

| | | | |
|---|---|---|---|
| DE | 3838593 C1 * | 5/1990 | |
| DE | 4235736 C1 * | 3/1994 | |
| DE | 199 47 331 A1 | 4/2001 | |
| EP | 1 106 243 A2 | 6/2001 | |
| EP | 1 149 627 A2 | 10/2001 | |
| JP | 2000-116675 | 4/2000 | |
| JP | 2000-117080 | 4/2000 | |

* cited by examiner

*Primary Examiner*—Charles E. Cooley
(74) *Attorney, Agent, or Firm*—Oblon, Spivak, McClelland, Maier & Neustadt, P.C.

(57) ABSTRACT

A stirring mixer for a dental impression material to decrease bubbles to be generated in a mixed dental impression material and the material to be left in a tubular main body, the mixer has a tubular main body wherein a discharging portion is provided following the mixing portion via a throttling portion from an injecting portion to which two pastes are injected, and a stirring rod with protruding stirring blades is rotated by a motor, leading ends of $1^{st}$ blades are positioned in a largest diameter portion of the throttling portion, leading ends of $2^{nd}$, $3^{rd}$ and $4^{th}$ blades are positioned in an inner diameter portion of the mixing portion, $1^{st}$ blade in a rotational direction and interval between $3^{rd}$ and $4^{th}$ blades is wider than that between the other adjacent blades, and opposing faces of $3^{rd}$ and $4^{th}$ blade to each other bulge towards the other blades.

2 Claims, 2 Drawing Sheets

STIRRING MIXER FOR DENTAL IMPRESSION MATERIAL

TECHNICAL FIELD

The present invention relates to a stirring mixer for a dental impression material which stirs the dental impression material comprising two kinds of pastes by a stirring rod and discharges the dental impression materials in a mixed state when the dental impression material is injected into a tubular main body, and in more detail, relates to a stirring mixer for a dental impression material in which bubbles or the like are hard to be generated at the initial stage of use thereof, and the waste of the dental impression material left within the tubular main body after using is decreased.

BACKGROUND OF THE INVENTION

In the case of mixing the dental impression material comprising a base material paste and a hardening material paste, it is convenient to inject each of the pastes to a transparent or semi-transparent tubular main body to which a stirring rod with a stirring blade is attached, and mix the dental impression material by rotating the stirring rod by an electric motor or the like.

In the case of using the stirring mixer for the dental impression material comprising the tubular main body and the stirring rod mentioned above, each of the pastes is injected to an empty tubular main body at a time of starting the use thereof followed by the mixing. Accordingly, there is a problem that the bubbles tend to enter into the mixed dental impression material.

Further, after use, a lot of mixed dental impression material is left within the tubular main body, and the remaining dental impression material is hardened and can not be reused and is to be disposed. Accordingly, there is a problem that a lot of mixed dental impression material is wasted.

As the stirring mixer for the dental impression material mentioned above, there is a mixer for adjusting a paste by mixing different amounts of components, comprising a container which has a horizontal axis, is provided with an intake port portion for each of the components in a rear terminal end and is provided with an injection portion in a front face, and a mixing chamber which is formed in the container, in which a delay chamber is provided between one of the intake portions within the container and the mixing chamber, and is formed so as to extend in an arc shape around the horizontal shaft in such a manner that a path flowing the component taken in from the one intake port is elongated is disclosed in Japanese patent laid-open No. 2000-117080. However, in this mixer, since one component is passed via the long arc-extended delay chamber of the path, there is a defect that an amount of the paste which is disposed after being used is increased.

Further, as the paste mixing apparatus, there is a paste mixing apparatus comprising a paste supplying means for supplying two pastes, a casing having a tubular main portion arranged in a downstream side of a leading end surface of the paste supplying means, a stirring member rotatably arranged within the casing, and a rotating means for stirring the stirring member, in which the stirring member includes an upstream stirring portion, a middle non-stirring portion and a downstream stirring portion, stirring blades protruding radially are formed in the upstream stirring portion and the downstream stirring portion, however, no stirring blade exists in the middle non-stirring portion. In this paste mixing apparatus, since the paste just after being injected is not mixed, the paste is hard to be hardened and is hard to be disposed after being used. Accordingly, there is an aspect in which an extension portion for mixing the paste mentioned above is attached to the stirring blade is disclosed in Japanese patent laid-open No. 2000-116675. However, the paste mixing apparatus is only designed to easily dispose the remaining paste after being used, but can not decrease the amount of the disposed paste. Further, the paste mixing apparatus does not cope with the problem that the bubbles tend to make an intrusion into the paste when the apparatus is put to use thereof.

SUMMARY OF THE INVENTION

An object of the present invention is to provide a stirring mixer for a dental impression material in which bubbles or the like are hard to be generated in the dental impression material which is stirred so as to be mixed when it is put to use, and an amount of the mixed dental impression material which is left within a tubular main body after use is decreased to avoid waste.

As a result of an intensive research made by the inventors of the present invention for the purpose of achieving the object mentioned above, the inventors have found the following matters. In the case that a stirring mixer for a dental impression material is constituted by a tubular main body in which a discharging portion having a small inner diameter and formed in a cylindrical shape is provided following to a kneading portion having a middle inner diameter and formed in a cylindrical shape via a throttling portion formed in a tapered circular truncated cone tubular shape from an injecting portion having a large inner diameter and formed in a cylindrical shape to which two kinds of pastes constituting the dental impression material are injected into the tubular main body, and a stirring rod which is provided with plural sets of stirring blades comprising first stirring blades, second stirring blades, third stirring blades and fourth stirring blades which are arranged sequentially on an approximately cylindrical outer surface from an injection portion side of the tubular main body, in a protruding manner, and is rotated by a motor in a state of being attached within the tubular main body, a leading end of the first stirring blade is positioned in a largest diameter portion of the throttling portion, and each of the first stirring blades is formed in a tapered curved shape as a back face side of the stirring rod in a rotational direction extends to a leading end, it is possible to decrease the stirring in the mixing portion by means of the first stirring blades having the shape applying a high stirring effect and corresponding to the tapered circular truncated cone tubular shaped throttling portion for serving to smoothly deliver two kinds of pastes to the mixing portion, and it is possible to shorten the mixing portion. Accordingly, it is possible to decrease the amount of the mixed dental impression material left within the tubular main body after being used. Further, in the case that an interval between the third stirring blade and the fourth stirring blade is set to be wider than an interval between the other adjacent stirring blades, and opposing faces of the third stirring blade and the fourth stirring blade to each other are formed in a shape bulging toward the other stirring blade, a large space is formed between the third stirring blade and the fourth stirring blade, and the opposing faces of the third stirring blade and the fourth stirring blade to each other bulge toward the space. Accordingly, the dental impression material having a high viscosity smoothly flows into the space without involving the air within the tubular main body, and the space is completely filled with the mixed dental impression material, whereby the air in the tubular main body is completely pushed out toward the discharging portion. Then, the present invention is completed by the inventors who have researched a means for preventing the bubbles from being intruded into the mixed dental impression material at the initial stage of use thereof.

In other words, in accordance with the present invention, there is provided a stirring mixer for a dental impression material constituted by a tubular main body in which a discharging portion having a small inner diameter and formed in a cylindrical shape is provided following to a kneading portion having a middle inner diameter and formed in a cylindrical shape via a throttling portion formed in a tapered circular truncated cone tubular shape from an injecting portion having a large inner diameter and formed in a cylindrical shape and two kinds of pastes constituting the dental impression material are injected into the tubular main body, and a stirring rod which is provided with plural sets of stirring blades on an approximately cylindrical outer surface in a protruding manner, and is rotated by a motor in a state of being attached within the tubular main body, wherein the stirring blades protruded from the outer surface of the stirring rod are formed in a state in which the stirring blades are arranged at a predetermined interval on a line parallel to an axial direction of the stirring rod and at a uniform interval in a circumferential direction of the stirring rod sequentially from a side of the injection portion of the tubular main body, and are constituted by first stirring blades in which leading ends are positioned in a largest diameter portion of the throttling portion, second stirring blades third stirring blades and fourth stirring blades, which are respectively positioned within the kneading portion of the tubular main body and in which leading ends are positioned in an inner diameter portion of the kneading portion, and wherein each of the first stirring blades is formed in a tapered curved shape as a back face side of the stirring rod extending to a leading end in a rotational direction, an interval between the third stirring blade and the fourth stirring blade is set to be wider than an interval between the other adjacent stirring blades, and opposing faces of the third stirring blade and the fourth stirring blade to each other bulge toward the other stirring blade.

Further, the inventors of the present invention have researched to find that in the case that an outer diameter of the stirring rod between the third stirring blade and the fourth stirring blade is smaller than an outer diameter of the stirring blade between the other stirring blades, the mixed dental impression material having a viscosity can easily and smoothly flows into a portion between the third stirring rod and the fourth stirring blade, the structure thereof is preferable.

In accordance with the present invention, the stirring mixer for the dental impression material is constituted by the tubular main body in which the discharging portion having the small inner diameter and formed in the cylindrical shape is provided following the kneading portion having the middle inner diameter and formed in the cylindrical shape via the throttling portion formed in the tapered circular truncated cone tubular shape from the injecting portion having the large inner diameter and formed in the cylindrical shape and two kinds of pastes constituting the dental impression material are injected into the tubular main body, and the stirring rod which is provided with plural sets of stirring blades on the approximately cylindrical outer surface in the protruding manner, and is rotated by the motor in a state of being attached within the tubular main body, and the stirring blades protruded from the outer surface of the stirring rod are formed in a state in which the stirring blades are arranged at the predetermined interval on the line parallel to the axial direction of the stirring rod and at the uniform interval in the circumferential direction of the stirring rod sequentially from the side of the injection portion of the tubular main body, and are constituted by the first stirring blades in which the leading ends are positioned in the largest diameter portion of the throttling portion, the second stirring blades the third stirring blades and the fourth stirring blades, which are respectively positioned within the kneading portion of the tubular main body and in which the leading ends are positioned in the inner diameter portion of the kneading portion, and the first stirring blades is provided such that the leading ends are positioned in the largest diameter portion of the throttling portion. Accordingly, since two kinds of pastes are stirred by the first stirring blades in the tapered circular truncated cone tubular shaped throttling portion for serving to smoothly delivering of two kinds of pastes to the stirring portion, and each of the first stirring blades is curved such that the back face side is tapered, the paste having a high viscosity tends to move around the back face side so as to increase a stirring effect. Further, since the leading end of the first stirring blade has a sufficient length to be positioned in the largest diameter portion of the throttle portion, two kinds of pastes are delivered to the mixing portion in a state of being mixed uniformly to certain extent, so that the stirring in the kneading portion is decreased and it is possible to decrease the kneading portion. Accordingly, it is possible to decrease an amount of the mixed dental impression material which is left in the tubular main body after the use thereof. Further, since the interval between the third stirring blade and the fourth stirring blade is set to be wider than the interval between the other adjacent stirring blades, and the opposing faces of the third stirring blade and the fourth stirring blade to each other bulge toward the other stirring blade, the large space is formed between the third stirring blade and the fourth stirring blade which are positioned in the discharging portion side of the tubular main body in the stirring blades arranged in the outer face of the stirring rod, and the opposing faces of the third stirring blade and the fourth stirring blade to each other bulge toward the space, it is possible to inject the mixed dental impression material having the viscosity smoothly without involving the air within the tubular main body, and the space is completely filled with the mixed dental impression material, whereby the air in the tubular main body is completely pushed out toward the discharging portion. Accordingly, it is possible to prevent the bubbles from making an intrusion into the mixed dental impression material at a time of starting using.

Further, in the case that the outer diameter of the stirring rod between the third stirring blade and the fourth stirring blade is smaller than the outer diameter of the stirring blade between the other stirring blades, a larger space can be further formed between the third stirring blade and the fourth stirring blade. Accordingly, it is possible for the mixed dental impression material of a high viscosity to flow smoothly.

DESCRIPTION OF THE PREFERRED EMBODIMENT

Figure 1:
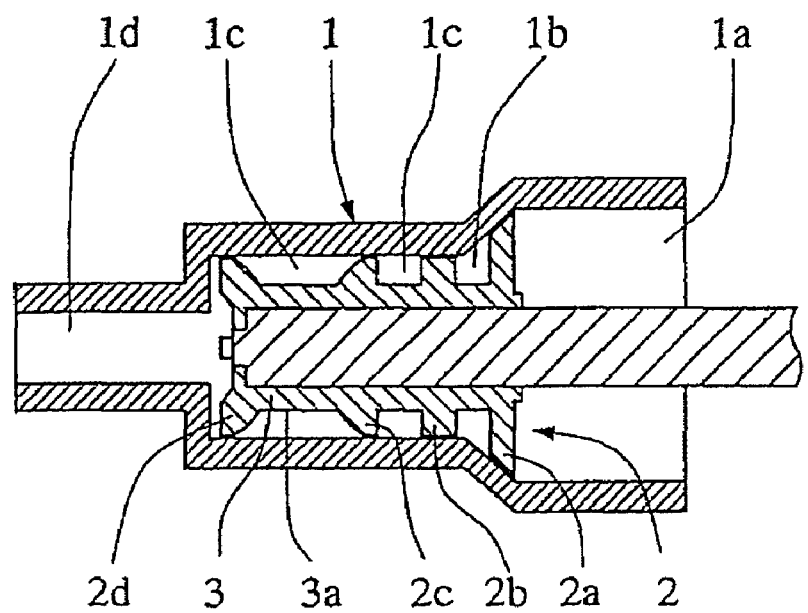
FIG. 1 is an elevational cross-sectional view of an embodiment of a stirring mixer for a dental impression material in accordance with the present invention.

A description will be explained in detail of a stirring mixer for a dental impression material in accordance with the present invention with reference to the accompanying drawings.

In the drawings, reference numeral 1 denotes a tubular main body in which a discharging portion 1d having a small inner diameter and formed in a cylindrical shape is provided following a kneading portion 1c having a middle inner diameter and formed in a cylindrical shape via a throttling portion 1b formed in a tapered circular truncated cone tubular shape from an injecting portion 1a having a large inner diameter, formed in a cylindrical shape and to which two kinds of pastes constituting the dental impression material are injected. The tubular main body 1 is preferably molded by a transparent or semi-transparent plastic or the like so that a state of the paste can be recognized.

Reference numeral 2 denotes plural sets of stirring blades which are protruded from an outer surface 3a of a stirring rod 3 to be referred to later. The stirring blade 2 is constituted by first stirring blades 2a in which leading ends are positioned in a largest diameter portion of the throttling portion 1b, second stirring blades 2b, third stirring blades 2c and fourth stirring blades 2d which are respectively positioned within the kneading portion 1c of the tubular main body 1 and in which leading ends are positioned in an inner diameter portion of the kneading portion 1c. These stirring blades are formed in a state of being arranged on a line parallel to an axial direction of the stirring rod 3 at a predetermined interval and at a uniform interval in a circumferential direction of the stirring rod 3 sequentially from an injecting portion 1a of the tubular main body 1.

The leading end of the first stirring blade 2a is positioned in the largest diameter portion of the throttling portion 1b for the purpose of stirring two kinds of pastes by the throttling portion 1b of the tubular main body 1, and each of the first stirring blades 2a is curved in a tapered shape the back face side of the stirring rod 3 in a rotational direction extends toward the leading end for the purpose of improving the stirring effect.

A plurality of second stirring blades 2b may be arranged on a line parallel to the axial direction of the stirring rod 3 in correspondence to the length of the stirring rod 3 as far as the second stirring blades 2b are arranged between the first stirring blades 2a and the third stirring blades 2c.

Further, the opposing surfaces of the third stirring blade 2c and the fourth stirring blade 2d to each other which are positioned in the discharging portion 1d of the tubular main body 1 bulge to the other stirring blades 2d and 2c side so as to smoothly flow two kinds of pastes while mixing without involving the air within the tubular main body 1, and the interval between the third stirring blade 2c and the fourth stirring blade 2d is set to be wider than the interval between the other adjacent stirring blades 2a and 2b, or the interval between the stirring blades 2b and 2b in the case that a plurality of second stirring blades 2b are arranged, and between the stirring blades 2b and 2c so as to completely fill the portion between the third stirring blade 2c and the fourth stirring blade 2d with the mixed dental impression material and completely push out the air in the tubular main body 1 to the discharging portion 1d. Further, in the case that the molding is carried out such that the outer diameter of the stirring rod 3 between the third stirring blade 2c and the fourth stirring blade 2d is smaller than the outer diameter of the stirring rod 3 between the other adjacent stirring blades, a further large space is formed between the third stirring blade 2c and the fourth stirring blade 2d. Accordingly, it is possible to smoothly inject the mixed dental impression material having a high viscosity and such structure is preferable.

Reference numeral 3 denotes a stirring rod in which the plural sets of stirring blades 2 are protruded on an approximately cylindrical outer surface 3a and which is rotated by a motor in a state of being attached to the cylindrical main body 1. It is preferable that the stirring rod 3 is integrally molded by a synthetic resin or the like together with the stirring blades 2 protruded from the outer surface 3a because it is inexpensively and easily manufactured.

As the stirring mixer for the dental impression material in accordance with the present invention having the structure mentioned above, there is an aspect shown in FIG. 1. In this aspect, the stirring rod 3 is arranged within the tubular main body 1 in a state in which a rotary shaft of the motor is inserted to a center.

Figure 2:
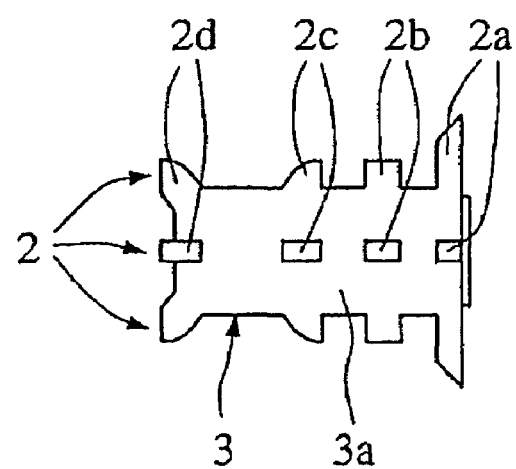
FIG. 2 is an elevational view of a stirring rod in FIG. 1.
Figure 3:
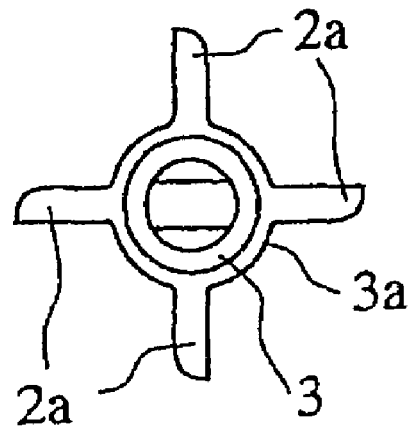
FIG. 3 is a right side view of the stirring rod in FIG. 1.

Further, the plural sets of stirring blades 2 protruded from the outer face 3a of the stirring rod 3 is structured such that the leading ends of the first stirring blades 2a are positioned in the largest diameter portion of the throttling portion 1b, the second stirring blades 2b, the third stirring blades 2c and the fourth stirring blades 2d are respectively positioned within the kneading portion 1c of the tubular main body 1 and the leading ends thereof are positioned in the inner diameter portion of the kneading portion 1c. Further, as shown in FIGS. 2 and 3, the stirring blades 2 are provided on a line parallel to the axial direction of the stirring rod 3 and are arranged at the uniform interval in the circumferential direction of the stirring rod 3. In the drawings, every four stirring blades 2 are provided in the circumferential direction of the stirring rod 3, however, the structure is not limited to this, and the number thereof may be determined in correspondence to a nature of the paste constituting the dental impression material to be used.

In the case of actually using the stirring mixer for the dental impression material in accordance with this aspect, first, two kinds of pastes are continuously injected to the injecting portion 1a of the tubular main body 1 at a fixed speed in a state of rotating the stirring rod 3. In this case, two kinds of pastes are continuously injected at the fixed speed because a uniformly mixed dental impression material is obtained by pushing out the paste within the tubular main body 1 toward the discharging portion 1d by the sequentially injected paste at an approximately fixed speed so as to always fix the mixing time. Next, two kinds of pastes injected to the injecting portion 1a are stirred by the sufficiently long first stirring blades 2a in which the leading end is positioned in the largest diameter portion of the throttling portion 1b in the tapered circular truncated cone tubular shape throttling portion 1b, and are pushed out to the kneading portion 1c in a state of being mixed uniformly to some extent. Further, the paste pushed out to the kneading portion 1c is further stirred by the second stirring blades 2b, the third stirring blades 2c and the fourth stirring blades 2d, and is pushed out to the outer portion from the discharging portion 1d in a state of being sufficiently mixed.

Figure 4:
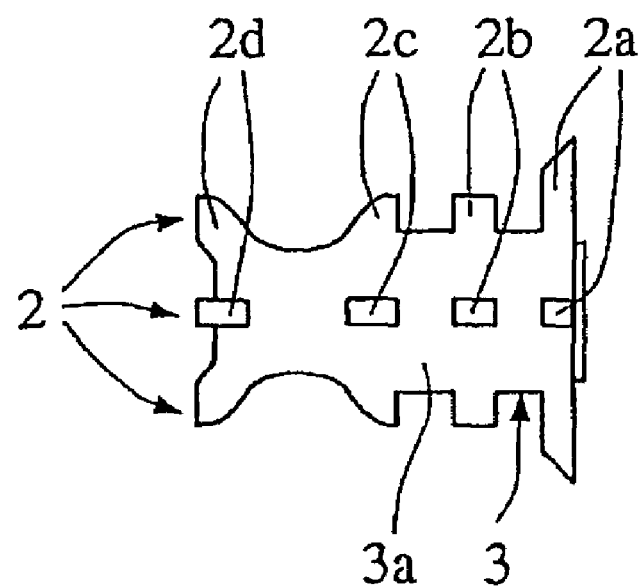
FIG. 4 is an elevational view showing another embodiment of the stirring rod.

In this case, in the kneading portion 1c, since the interval between the third stirring blades 2c and the fourth stirring blades 2d is set to be wider than the interval between the other adjacent stirring blades 2a and 2b and between the other adjacent stirring blades 2b and 2c, and the opposing surfaces of the third stirring blades 2c and the fourth stirring blades 2d to each other bulge to the other stirring blades 2d and 2c side, the large space is formed between the third stirring blades 2c and the fourth stirring blades 2d which are positioned in the side of the discharging portion 1d of the tubular main body 1 in the stirring blades 2 arranged in the outer surface 3a of the stirring rod 3, and the opposing faces of the third stirring blades 2c and the fourth stirring blades 2d to each other bulge toward the large space. Accordingly, the mixed dental impression material having the viscosity can be smoothly flow into the space without involving the air within the tubular main body 1, and the space is completely filled with the mixed dental impression material, whereby the air in the tubular main body 1 is completely pushed out toward the discharging portion 1d. Therefore, the bubbles are hard to be intruded into the mixed dental impression material at the initial stage of use thereof. Further, as shown in FIG. 4, in the case that the outer diameter of the stirring rod 3 between the third stirring blades 2c and the fourth stirring blades 2d is smaller than the outer diameter of the stirring rod 3 between the other stirring blades 2a and 2b and between the other stirring blades 2b and 2c, the larger space is further formed between the third stirring blades 2c and the fourth stirring blades 2d. Accordingly, it is possible for the mixed dental impression material of high viscosity to flow smoothly.

What is claimed is:

1. A stirring mixer for a dental impression material comprising:

a tubular main body (1) in which a discharging portion (1d) having a small inner diameter and formed in a cylindrical shape is provided following to a kneading portion (1c) having a middle inner diameter and formed in a cylindrical shape via a throttling portion (1b) formed in a tapered circular truncated cone tubular shape from an injecting portion (1a) having a large inner diameter and formed in a cylindrical shape to which two kinds of pastes constituting the dental impression material are injected; and a stirring rod (3) which is provided with plural sets of stirring blades (2) on an approximately cylindrical outer surface (3a) in a protruding manner, and is rotated by a motor in a state of being attached within the tubular main body (1), wherein the stirring blades (2) protruded from the outer surface (3a) of said stirring rod are formed in a state in which the stirring blades are arranged at a predetermined interval on a line parallel to an axial direction of said stirring rod (3) and at a uniform interval in a circumferential direction of said stirring rod (3) sequentially from a side of the injecting portion (1a) of said tubular main body (1) and are constituted by first stirring blades (2a) in which leading ends are positioned in a largest diameter portion of said throttling portion (1b), second stirring blades (2b) third stirring blades (2c) and fourth stirring blades (2d), which are respectively positioned within the kneading portion (1c) of said tubular main body (1) and in which leading ends are positioned in an inner diameter portion of said kneading portion (1c), and wherein each of the first stirring blades (2a) is formed in a tapered curved shape with a back face side of said stirring rod (3) extending to a leading end in a rotational direction, an interval between the third stirring blade (2c) and the fourth stirring blade (2d) is set to be wider than an interval between the other adjacent stirring blades (between 2a and 2b and between 2b and 2c), and opposing faces of the third stirring blade (2c) and the fourth stirring blade (2d) to each other bulge toward the other stirring blades (2d, 2c).

2. A stirring mixer for a dental impression material as claimed in claim 1, wherein an outer diameter of the stirring rod (3) between the third stirring blade (2c) and the fourth stirring blade (2d) is smaller than an outer diameter of the stirring rod (3) between the other stirring blades (between 2a and 2b and between 2b and 2c).

* * * * *